US007853307B2

(12) United States Patent
Edwards

(10) Patent No.: US 7,853,307 B2
(45) Date of Patent: *Dec. 14, 2010

(54) METHODS, APPARATUSES, AND SYSTEMS USEFUL IN CONDUCTING IMAGE GUIDED INTERVENTIONS

(75) Inventor: Jerome R. Edwards, Nashville, TN (US)

(73) Assignee: Veran Medical Technologies, Inc., St. Louis, MO (US)

( * ) Notice: Subject to any disclaimer, the term of this patent is extended or adjusted under 35 U.S.C. 154(b) by 28 days.

This patent is subject to a terminal disclaimer.

(21) Appl. No.: 12/146,738

(22) Filed: Jun. 26, 2008

(65) Prior Publication Data

US 2008/0298655 A1    Dec. 4, 2008

Related U.S. Application Data

(63) Continuation of application No. 10/649,600, filed on Aug. 26, 2003, now Pat. No. 7,398,116.

(60) Provisional application No. 60/494,268, filed on Aug. 11, 2003.

(51) Int. Cl.
*A61B 5/05* (2006.01)

(52) U.S. Cl. ........................... 600/424; 600/426

(58) Field of Classification Search ................. 600/424, 600/426, 407, 414
See application file for complete search history.

(56) References Cited

U.S. PATENT DOCUMENTS

| 5,053,042 | A | 10/1991 | Bidwell |
| 5,158,088 | A | 10/1992 | Nelson et al. |
| 5,186,174 | A | 2/1993 | Schlondorff et al. |
| 5,251,165 | A | 10/1993 | James, III |
| 5,251,635 | A | 10/1993 | Dumoulin et al. |
| 5,265,610 | A | 11/1993 | Darrowm et al. |
| 5,348,011 | A | 9/1994 | NessAiver |
| 5,377,678 | A | 1/1995 | Dumoulin et al. |
| 5,391,199 | A | 2/1995 | Ben-Haim |
| 5,483,691 | A | 1/1996 | Heck et al. |
| 5,483,961 | A | 1/1996 | Kelly et al. |

(Continued)

FOREIGN PATENT DOCUMENTS

DE    19725137 C    1/1999

(Continued)

*Primary Examiner*—Long V Le
*Assistant Examiner*—Jacqueline Cheng
(74) *Attorney, Agent, or Firm*—Bryan Cave LLP

(57) ABSTRACT

Methods, apparatuses, and systems relating to image guided interventions on dynamic tissue. One embodiment is a method that includes creating a dataset that includes images, one of the images depicting a non-tissue internal reference marker, being linked to non-tissue internal reference marker positional information, and being at least 2-dimensional. Another embodiment is a method that includes receiving a position of an instrument reference marker coupled to an instrument; transforming the position into image space using a position of a non-tissue internal reference marker implanted in a patient; and superimposing a representation of the instrument on an image in which the non-tissue internal reference marker appears. Computer readable media that include machine readable instructions for carrying out the steps of the disclosed methods. Apparatuses, such as integrated circuits, configured to carry out the steps of the disclosed methods. Systems that include devices configured to carry out steps of the disclosed methods.

20 Claims, 10 Drawing Sheets

U.S. PATENT DOCUMENTS

| | | |
|---|---|---|
| 5,577,502 A | 11/1996 | Darrow et al. |
| 5,581,183 A | 12/1996 | Lindstedt et al. |
| 5,644,612 A | 7/1997 | Moorman et al. |
| 5,671,739 A | 9/1997 | Darrow et al. |
| 5,718,241 A | 2/1998 | Ben-Haim et al. |
| 5,730,129 A | 3/1998 | Darrow et al. |
| 5,740,808 A | 4/1998 | Panescu et al. |
| 5,765,561 A | 6/1998 | Chen et al. |
| 5,769,789 A * | 6/1998 | Wang et al. .................. 600/414 |
| 5,769,861 A | 6/1998 | Vilsmeier |
| 5,787,886 A | 8/1998 | Kelly et al. |
| 5,803,089 A | 9/1998 | Ferre et al. |
| 5,840,025 A | 11/1998 | Ben-Haim |
| 5,868,673 A | 2/1999 | Vesely |
| 5,978,696 A | 11/1999 | VomLehn et al. |
| 6,016,439 A | 1/2000 | Acker |
| 6,019,724 A | 2/2000 | Gronningsaeter et al. |
| 6,026,173 A | 2/2000 | Svenson et al. |
| 6,078,175 A | 6/2000 | Foo |
| 6,122,538 A | 9/2000 | Sliwa, Jr. et al. |
| 6,144,875 A | 11/2000 | Schweikard |
| 6,167,296 A | 12/2000 | Shahidi |
| 6,173,201 B1 | 1/2001 | Front |
| 6,198,959 B1 | 3/2001 | Wang |
| 6,201,987 B1 | 3/2001 | Dumoulin |
| 6,226,543 B1 | 5/2001 | Gilboa et al. |
| 6,226,548 B1 | 5/2001 | Foley et al. |
| 6,233,476 B1 | 5/2001 | Strommer et al. |
| 6,235,038 B1 | 5/2001 | Hunter et al. |
| 6,236,875 B1 | 5/2001 | Bucholz et al. |
| 6,246,896 B1 | 6/2001 | Dumoulin |
| 6,246,898 B1 | 6/2001 | Vesely et al. |
| 6,267,769 B1 | 7/2001 | Truwit |
| 6,275,560 B1 | 8/2001 | Blake |
| 6,282,442 B1 | 8/2001 | DeStefano |
| 6,285,902 B1 | 9/2001 | Kienzle |
| 6,298,259 B1 | 10/2001 | Kucharczyk et al. |
| 6,314,310 B1 | 11/2001 | Ben-Haim et al. |
| 6,314,311 B1 | 11/2001 | Williams |
| 6,314,312 B1 | 11/2001 | Wessels et al. |
| 6,317,616 B1 | 11/2001 | Glossop |
| 6,317,619 B1 | 11/2001 | Boernert |
| 6,330,356 B1 | 12/2001 | Sundareswaran et al. |
| 6,332,089 B1 | 12/2001 | Acker et al. |
| 6,332,891 B1 | 12/2001 | Himes |
| 6,335,623 B1 | 1/2002 | Damadian et al. |
| 6,340,363 B1 | 1/2002 | Bolger et al. |
| 6,347,240 B1 | 2/2002 | Foley et al. |
| 6,348,058 B1 | 2/2002 | Melkent et al. |
| 6,351,573 B1 | 2/2002 | Schneider |
| 6,351,659 B1 | 2/2002 | Vilsmeier |
| 6,361,759 B1 | 3/2002 | Frayne et al. |
| 6,362,821 B1 | 3/2002 | Gibson |
| 6,368,331 B1 | 4/2002 | Front et al. |
| 6,369,571 B1 | 4/2002 | Damadian et al. |
| 6,379,302 B1 | 4/2002 | Kessman et al. |
| 6,381,485 B1 | 4/2002 | Hunter et al. |
| 6,402,762 B2 | 6/2002 | Hunter |
| 6,421,551 B1 | 7/2002 | Kuth et al. |
| 6,424,856 B1 | 7/2002 | Vilsmeier et al. |
| 6,425,865 B1 | 7/2002 | Salcudean et al. |
| 6,430,430 B1 | 8/2002 | Gosche |
| 6,434,415 B1 | 8/2002 | Foley et al. |
| 6,434,507 B1 | 8/2002 | Clayton et al. |
| 6,437,571 B1 | 8/2002 | Danby et al. |
| 6,442,417 B1 | 8/2002 | Shahidi et al. |
| 6,445,186 B1 | 9/2002 | Damadian et al. |
| 6,445,943 B1 | 9/2002 | Ferre et al. |
| 6,455,182 B1 | 9/2002 | Silver |
| 6,461,372 B1 | 10/2002 | Jensen |
| 6,468,265 B1 | 10/2002 | Evans et al. |
| 6,469,508 B1 | 10/2002 | Damadian et al. |
| 6,470,066 B2 | 10/2002 | Takagi |
| 6,470,207 B1 | 10/2002 | Simon et al. |
| 6,473,635 B1 | 10/2002 | Rasche |
| 6,477,400 B1 | 11/2002 | Barrick |
| 6,478,793 B1 | 11/2002 | Cosman |
| 6,478,802 B2 | 11/2002 | Kienzle |
| 6,483,948 B1 | 11/2002 | Spink |
| 6,484,049 B1 | 11/2002 | Seeley et al. |
| 6,485,413 B1 | 11/2002 | Boppart et al. |
| D466,609 S | 12/2002 | Glossop |
| 6,490,467 B1 | 12/2002 | Bucholz et al. |
| 6,490,475 B1 | 12/2002 | Seeley et al. |
| 6,490,477 B1 | 12/2002 | Zylka et al. |
| 6,491,699 B1 | 12/2002 | Henderson et al. |
| 6,491,702 B2 | 12/2002 | Heilbrun et al. |
| 6,493,574 B1 | 12/2002 | Ehnholm et al. |
| 6,496,007 B1 | 12/2002 | Damadian et al. |
| 6,501,981 B1 | 12/2002 | Schweikard et al. |
| 6,504,893 B1 | 1/2003 | Flohr et al. |
| 6,504,894 B2 | 1/2003 | Pan et al. |
| 6,517,485 B2 | 2/2003 | Torp et al. |
| 6,527,443 B1 | 3/2003 | Vilsmeier et al. |
| 6,535,756 B1 | 3/2003 | Simon et al. |
| 6,538,634 B1 | 3/2003 | Chui et al. |
| 6,539,127 B1 | 3/2003 | Roche et al. |
| 6,541,973 B1 | 4/2003 | Danby et al. |
| 6,544,041 B1 | 4/2003 | Damadian |
| 6,547,782 B1 | 4/2003 | Taylor |
| 6,558,333 B2 | 5/2003 | Gilboa et al. |
| 6,567,687 B2 | 5/2003 | Front et al. |
| 6,580,938 B1 | 6/2003 | Acker |
| 6,584,174 B2 | 6/2003 | Schubert et al. |
| 6,584,339 B2 | 6/2003 | Galloway, Jr. et al. |
| 6,591,130 B2 | 7/2003 | Shahidi |
| 6,606,513 B2 | 8/2003 | Lardo et al. |
| 6,609,022 B2 | 8/2003 | Vilsmeier et al. |
| 6,636,757 B1 | 10/2003 | Jascob et al. |
| 6,650,924 B2 | 11/2003 | Kuth et al. |
| 6,666,579 B2 | 12/2003 | Jensen |
| 6,674,833 B2 | 1/2004 | Shahidi et al. |
| 6,675,032 B2 | 1/2004 | Chen et al. |
| 6,675,033 B1 | 1/2004 | Lardo et al. |
| 6,687,531 B1 | 2/2004 | Ferre et al. |
| 6,690,960 B2 | 2/2004 | Chen et al. |
| 6,694,167 B1 | 2/2004 | Ferre et al. |
| 6,697,664 B2 | 2/2004 | Kienzle, III et al. |
| 6,711,429 B1 | 3/2004 | Gilboa et al. |
| 6,714,629 B2 | 3/2004 | Vilsmeier |
| 6,714,810 B2 | 3/2004 | Grzeszczuk et al. |
| 6,725,080 B2 | 4/2004 | Melkent et al. |
| 6,738,656 B1 | 5/2004 | Ferre et al. |
| 6,772,002 B2 | 8/2004 | Schmidt et al. |
| 6,774,624 B2 | 8/2004 | Anderson et al. |
| 6,782,287 B2 | 8/2004 | Grzeszczuk et al. |
| 6,796,988 B2 | 9/2004 | Melkent et al. |
| 6,823,207 B1 | 11/2004 | Jensen et al. |
| 6,826,423 B1 | 11/2004 | Hardy et al. |
| 6,850,794 B2 | 2/2005 | Shahidi |
| 6,856,826 B2 | 2/2005 | Seeley et al. |
| 6,856,827 B2 | 2/2005 | Seeley et al. |
| 6,892,090 B2 | 5/2005 | Verard et al. |
| 6,898,303 B2 | 5/2005 | Armato, III et al. |
| 6,907,281 B2 | 6/2005 | Grzeszczuk |
| 6,920,347 B2 | 7/2005 | Simon et al. |
| 6,934,575 B2 | 8/2005 | Ferre et al. |
| 6,968,224 B2 | 11/2005 | Kessman et al. |
| 6,978,166 B2 | 12/2005 | Foley et al. |
| 7,015,859 B2 | 3/2006 | Anderson |
| 7,050,845 B2 | 5/2006 | Vilsmeier |
| 7,139,601 B2 | 11/2006 | Bucholz et al. |
| 7,153,297 B2 | 12/2006 | Peterson |
| 7,171,257 B2 | 1/2007 | Thomson |

| | | |
|---|---|---|
| 7,174,201 B2 | 2/2007 | Govari et al. |
| 7,260,426 B2 | 8/2007 | Schweikard et al. |
| 2001/0007918 A1 | 7/2001 | Vilsmeier et al. |
| 2001/0025142 A1 | 9/2001 | Wessels et al. |
| 2001/0029333 A1 | 10/2001 | Shahidi |
| 2001/0031919 A1 | 10/2001 | Strommer et al. |
| 2001/0031985 A1 | 10/2001 | Gilboa et al. |
| 2001/0036245 A1 | 11/2001 | Kienzle et al. |
| 2001/0041835 A1 | 11/2001 | Front et al. |
| 2002/0044631 A1 | 4/2002 | Graumann |
| 2002/0049375 A1 | 4/2002 | Strommer et al. |
| 2002/0049378 A1 | 4/2002 | Grzeszczuk et al. |
| 2002/0075994 A1 | 6/2002 | Shahidi et al. |
| 2002/0077543 A1 | 6/2002 | Grzeszczuk et al. |
| 2002/0077544 A1 | 6/2002 | Shahidi |
| 2002/0082492 A1 | 6/2002 | Grzeszczuk |
| 2002/0085681 A1 | 7/2002 | Jensen |
| 2002/0143317 A1 | 10/2002 | Glossop |
| 2002/0161295 A1 | 10/2002 | Edwards et al. |
| 2003/0000535 A1 | 1/2003 | Galloway, Jr. et al. |
| 2003/0004411 A1 | 1/2003 | Govari et al. |
| 2003/0016852 A1 | 1/2003 | Kaufman |
| 2003/0018251 A1 | 1/2003 | Solomon |
| 2003/0023161 A1 | 1/2003 | Govari et al. |
| 2003/0028091 A1 | 2/2003 | Simon et al. |
| 2003/0029464 A1 | 2/2003 | Chen et al. |
| 2003/0032878 A1 | 2/2003 | Shahidi |
| 2003/0040667 A1 | 2/2003 | Feussner et al. |
| 2003/0074011 A1 | 4/2003 | Gilboa et al. |
| 2003/0088179 A1 | 5/2003 | Seeley et al. |
| 2003/0125622 A1 | 7/2003 | Schweikard |
| 2003/0130576 A1 | 7/2003 | Seeley et al. |
| 2003/0139663 A1 | 7/2003 | Graumann |
| 2003/0208116 A1 | 11/2003 | Liang et al. |
| 2003/0208122 A1 | 11/2003 | Melkent et al. |
| 2003/0216631 A1 | 11/2003 | Bloch et al. |
| 2003/0220557 A1 | 11/2003 | Cleary et al. |
| 2004/0006268 A1 | 1/2004 | Gilboa et al. |
| 2004/0034300 A1 | 2/2004 | Verard et al. |
| 2004/0049121 A1 | 3/2004 | Yaron |
| 2004/0076259 A1 | 4/2004 | Jensen et al. |
| 2004/0092815 A1 | 5/2004 | Schweikard et al. |
| 2004/0097805 A1 | 5/2004 | Verard et al. |
| 2004/0097806 A1 | 5/2004 | Hunter et al. |
| 2004/0116803 A1 | 6/2004 | Jascob et al. |
| 2004/0122311 A1 | 6/2004 | Cosman |
| 2004/0138548 A1 | 7/2004 | Strommer et al. |
| 2004/0152970 A1 | 8/2004 | Hunter et al. |
| 2004/0152974 A1 | 8/2004 | Solomon |
| 2004/0193042 A1 | 9/2004 | Scampini et al. |
| 2004/0210125 A1 | 10/2004 | Chen et al. |
| 2005/0010099 A1 | 1/2005 | Raabe et al. |
| 2005/0027186 A1 | 2/2005 | Chen et al. |
| 2005/0033149 A1 | 2/2005 | Strommer et al. |
| 2005/0065433 A1 | 3/2005 | Anderson |
| 2005/0085793 A1 | 4/2005 | Glossop |
| 2005/0107688 A1 | 5/2005 | Strommer |
| 2005/0113809 A1 | 5/2005 | Melkent et al. |
| 2005/0143651 A1 | 6/2005 | Verard et al. |
| 2005/0169510 A1 | 8/2005 | Zuhars et al. |
| 2005/0182319 A1 | 8/2005 | Glossop |
| 2005/0197568 A1 | 9/2005 | Vass et al. |
| 2005/0203383 A1 | 9/2005 | Moctezuma de la Barrera et al. |
| 2005/0234335 A1 | 10/2005 | Simon et al. |
| 2005/0288574 A1 | 12/2005 | Thornton et al. |
| 2005/0288578 A1 | 12/2005 | Durlak |
| 2006/0004281 A1 | 1/2006 | Saracen |
| 2006/0025677 A1 | 2/2006 | Verard et al. |
| 2006/0045318 A1 | 3/2006 | Schoisswohl et al. |
| 2006/0050942 A1 | 3/2006 | Bertram et al. |
| 2006/0050988 A1 | 3/2006 | Kraus et al. |
| 2006/0058647 A1 | 3/2006 | Strommer et al. |
| 2006/0063998 A1 | 3/2006 | von Jako et al. |
| 2006/0064006 A1 | 3/2006 | Strommer et al. |
| 2006/0074292 A1 | 4/2006 | Thomson et al. |
| 2006/0074299 A1 | 4/2006 | Sayeh |
| 2006/0074304 A1 | 4/2006 | Sayeh |
| 2006/0079759 A1 | 4/2006 | Vaillant et al. |
| 2006/0084867 A1 | 4/2006 | Tremblay et al. |
| 2006/0093089 A1 | 5/2006 | Vertatschitsch et al. |
| 2006/0094958 A1 | 5/2006 | Marquart et al. |
| 2006/0106292 A1 | 5/2006 | Anderson |
| 2006/0116634 A1 | 6/2006 | Shachar |
| 2006/0122497 A1 | 6/2006 | Glossop |
| 2006/0173269 A1 | 8/2006 | Glossop |
| 2006/0173291 A1 | 8/2006 | Glossop |
| 2006/0189867 A1 | 8/2006 | Revie et al. |
| 2006/0247511 A1 | 11/2006 | Anderson |
| 2007/0032723 A1 | 2/2007 | Glossop |
| 2007/0038058 A1 | 2/2007 | West et al. |
| 2007/0066887 A1 | 3/2007 | Mire et al. |
| 2007/0110289 A1 | 5/2007 | Fu et al. |
| 2007/0129629 A1 | 6/2007 | Beauregard et al. |
| 2007/0167744 A1 | 7/2007 | Beauregard et al. |

FOREIGN PATENT DOCUMENTS

| | | |
|---|---|---|
| DE | 19829224 B | 1/2000 |
| DE | 19909816 | 5/2000 |
| DE | 10000937 B | 8/2001 |
| DE | 10136709 B | 2/2003 |
| DE | 10161160 | 6/2003 |
| DE | 102005010010 | 9/2005 |
| DE | 102004030836 | 1/2006 |
| DE | 102005038394 | 3/2006 |
| DE | 102005050286 | 4/2006 |
| DE | 102004058122 | 7/2006 |
| EP | 0 501 993 B1 | 9/1992 |
| EP | 0 869 745 B8 | 10/1998 |
| EP | 900048 B1 | 3/1999 |
| EP | 977510 | 2/2000 |
| EP | 1 079 240 A | 2/2001 |
| EP | 1152706 B1 | 11/2001 |
| EP | 1181897 | 2/2002 |
| EP | 1319368 | 6/2003 |
| EP | 1 374 792 A1 | 1/2004 |
| EP | 1 374 793 A1 | 1/2004 |
| EP | 1391181 | 2/2004 |
| EP | 1421913 | 5/2004 |
| EP | 1464285 B1 | 10/2004 |
| EP | 1 504 726 A1 | 2/2005 |
| EP | 1504713 | 2/2005 |
| EP | 1 519 140 A1 | 3/2005 |
| EP | 1 523 951 A2 | 4/2005 |
| EP | 1561423 | 8/2005 |
| EP | 1629774 | 3/2006 |
| EP | 1629789 | 3/2006 |
| FR | 2876273 | 4/2006 |
| WO | WO 95/01757 | 1/1995 |
| WO | WO 96/08209 A2 | 3/1996 |
| WO | WO 96/08209 A3 | 3/1996 |
| WO | WO96/10949 | 4/1996 |
| WO | WO 97/29699 | 8/1997 |
| WO | WO 97/29709 | 8/1997 |
| WO | WO98/36684 | 8/1998 |
| WO | WO99/16352 | 4/1999 |
| WO | WO99/43253 | 9/1999 |
| WO | WO00/16684 | 3/2000 |
| WO | WO00/28911 | 5/2000 |
| WO | WO00/47103 | 8/2000 |
| WO | WO00/49958 | 8/2000 |
| WO | WO00/57767 | 10/2000 |
| WO | WO00/69335 | 11/2000 |
| WO | WO01/01845 | 1/2001 |
| WO | WO01/37748 | 5/2001 |
| WO | WO01/62134 | 8/2001 |

| | | |
|---|---|---|
| WO | WO01/64124 | 9/2001 |
| WO | WO01/76496 | 10/2001 |
| WO | WO01/76497 | 10/2001 |
| WO | WO01/87136 | 11/2001 |
| WO | WO01/93745 | 12/2001 |
| WO | WO02/00093 | 1/2002 |
| WO | WO02/00103 | 1/2002 |
| WO | WO02/19936 | 3/2002 |
| WO | WO02/22015 | 3/2002 |
| WO | WO02/24051 | 3/2002 |
| WO | WO02/056770 | 7/2002 |
| WO | WO02/064011 | 8/2002 |
| WO | WO02/082375 | 10/2002 |
| WO | WO 02/098273 A2 | 12/2002 |
| WO | WO 2004/046754 A2 | 6/2004 |
| WO | WO2004/060157 | 7/2004 |
| WO | WO 2004/062497 A1 | 7/2004 |
| WO | WO2005/070318 | 8/2005 |
| WO | WO2005/077293 | 10/2005 |
| WO | WO2005/101277 | 10/2005 |
| WO | WO2005/111942 | 11/2005 |
| WO | WO 2006/002396 A2 | 1/2006 |
| WO | WO 2006/005021 A2 | 1/2006 |
| WO | WO2006/027781 | 3/2006 |
| WO | WO2006/039009 | 4/2006 |
| WO | WO2006/051523 | 5/2006 |
| WO | WO 2006/090141 A1 | 8/2006 |
| WO | WO 2007/002079 A2 | 1/2007 |
| WO | WO 2007/031314 A2 | 3/2007 |
| WO | WO 2007/062051 A2 | 5/2007 |
| WO | WO 2007/084893 A2 | 7/2007 |

\* cited by examiner

METHODS, APPARATUSES, AND SYSTEMS USEFUL IN CONDUCTING IMAGE GUIDED INTERVENTIONS

CROSS-REFERENCE(S) TO RELATED APPLICATION(S)

This application claims priority to and is a continuation of U.S. application Ser. No. 10/649,600, filed Aug. 26, 2003 by Jerome R. Edwards, entitled "METHODS, APPARATUSES, AND SYSTEMS USEFUL IN CONDUCTING IMAGE GUIDED INTERVENTIONS," now U.S. Pat. No. 7,398,116, which claims priority to U.S. Provisional Patent Application Ser. No. 60/494,268, filed Aug. 11, 2003 by Jerome R. Edwards, entitled "METHODS, APPARATUSES, AND SYSTEMS USEFUL IN CONDUCTING IMAGE GUIDED INTERVENTIONS," the entire contents of each are expressly incorporated by reference.

BACKGROUND OF THE INVENTION

1. Field of the Invention

The present invention is directed generally to computer readable media, apparatuses, systems, and methods that concern image guided medical procedures.

2. Description of Related Art

Image guided surgery (IGS), also known as image guided intervention (IGI), has become an established and proven technology field that enhances a physician's understanding of the location of his instruments within anatomy during therapy delivery. IGI has grown to include 2-dimensional (2-D) and 3-dimensional (3-D) applications. Virtual fluoroscopy as described in U.S. Pat. No. 6,470,207, Navigational Guidance via Computer Assisted Fluoroscopic Imaging, Simon et al, which is expressly incorporated by reference, discloses how to register the coordinate system of anatomy in a live operating theatre to that of a 2-D fluoroscopic image and then superimpose the real-time movements of instruments on that image as icons. U.S. Pat. No. 6,490,467, Surgical Navigation Systems Including Reference and Localization Frames, Bucholz et al., which is also expressly incorporated by reference, discloses how to register the coordinate system of anatomy in a live operating theatre to that of a 3-D magnetic resonance imaging (MRI) or computed tomography (CT) image volume and then superimpose the real-time movements of instruments on that image volume as icons. The techniques disclosed in these patents combined with other state of the art technologies have worked well in procedures involving static anatomy. Static anatomy is anatomy that does not move or has very minimal movement with respect to heart beat and respiration, such as the sinuses, long bones, brain, and individual vertebral bodies of the spine. The use of image guidance is fast approaching the standard of care in neurosurgical tumor resection, spinal implant placement, ear-nose-and-throat (ENT) surgery, and orthopedics.

However, IGI has not made significant inroads into medical procedures involving dynamic anatomy. Dynamic anatomy is anatomy that moves significantly with respect to heart beat and respiration, such as the heart, lungs, kidneys, liver, and blood vessels. IGI to date is limited mostly to use in static anatomy medical procedures primarily due to its usage of static imaging modalities such as single frame fluoroscopy, and single volume MRI and CT.

Imaging modalities do exist to capture dynamic anatomy. Modalities such as electrocardiogram (ECG)-gated MRI, ECG-gated CT and cinematography (CINE) fluoroscopy (e.g., looped CINE fluoroscopy) are readily available in hospitals worldwide. These dynamic imaging modalities can capture anatomy over an entire periodic cycle of movement by sampling the anatomy at several instances during its characteristic movement and then creating a set of image frames or volumes. The use of dynamic imaging modalities in IGI will allow IGI to transcend the boundaries of static anatomy and administer efficacy benefits to even more medical procedures.

U.S. Pat. No. 6,473,635, A Method of and Device for Determining the Position of A Medical Instrument, Rasche, which is expressly incorporated by reference, proposes using the ECG waveform emanating from a live patient in the operating theatre to continuously select from a set of images that were gated to ECG data. However, Rasche's proposal will not work when the patient exhibits an irregular ECG pattern due to the medical therapies that are being applied to him. Examples of induced ECG irregularity would occur during pacemaker and implantable cardioverter defibrillator lead placement and radiofrequency ablation of myocytes to cure tachycardia.

SUMMARY OF THE INVENTION

One embodiment is a method that includes creating a dataset that includes images, at least one of those images depicting a non-tissue internal reference marker, being linked to non-tissue internal reference marker positional information, and being at least 2-dimensional.

Another embodiment is a method that includes receiving a position of an instrument reference marker coupled to an instrument; transforming the position into image space using a position of a non-tissue internal reference marker implanted in a patient; and superimposing a representation of the instrument on an image in which the non-tissue internal reference marker appears.

Other embodiments of the present methods are disclosed below.

Other embodiments include computer readable media that include machine readable instructions for carrying out the steps of any of the present methods. Still other embodiments include apparatuses, such as integrated circuits, configured to carry out the steps of any of the present methods. Other embodiments include systems that include devices configured to carry out steps of the present methods.

BRIEF DESCRIPTION OF THE DRAWINGS

The following drawings demonstrate aspects of some of the present methods, apparatuses, and systems. They illustrate by way of example and not limitation. Like reference numbers refer to similar elements.

DESCRIPTION OF ILLUSTRATIVE EMBODIMENTS

Figure 1:
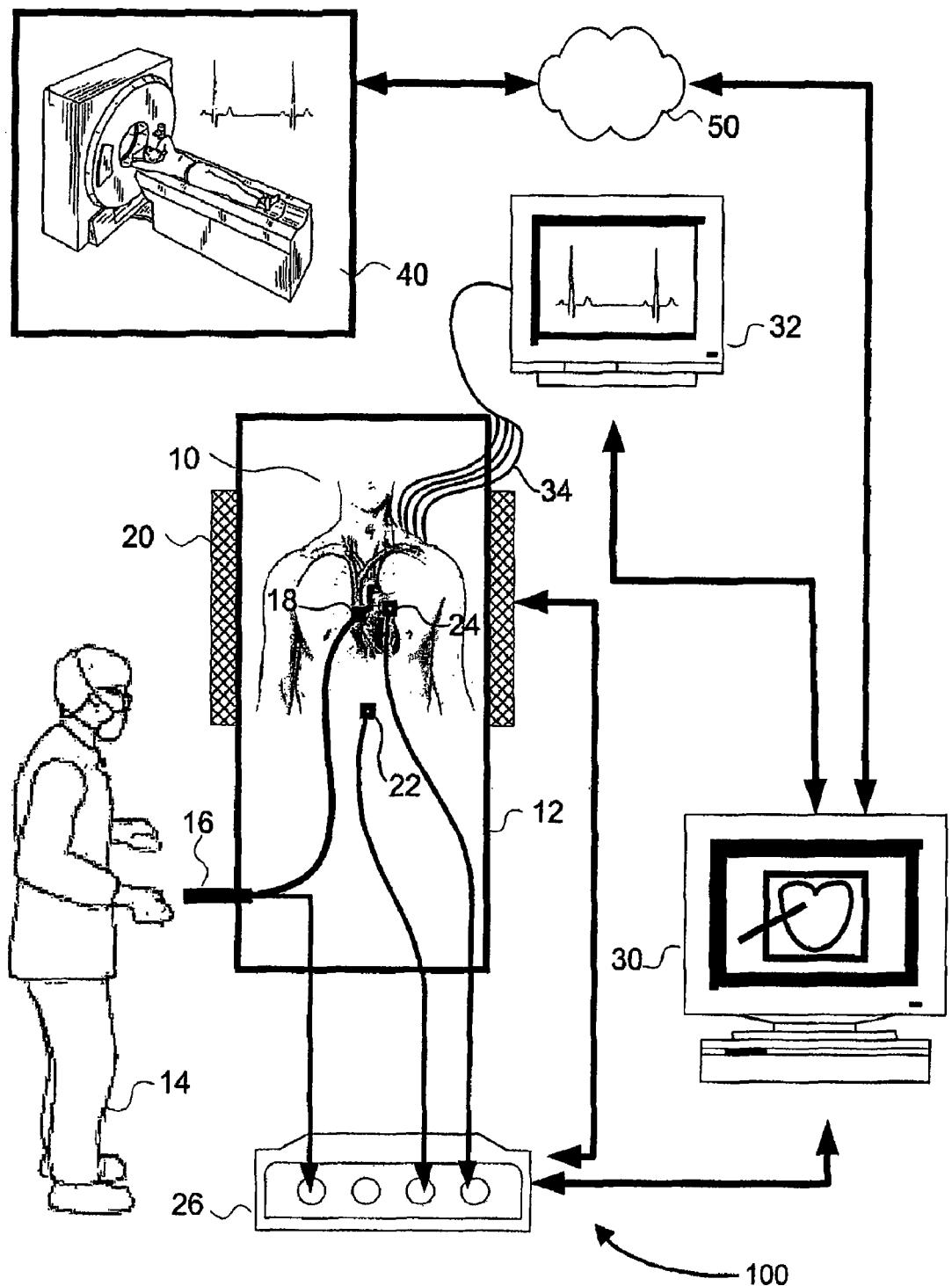
FIG. 1 shows the layout of a system that may be used to carry out image guided interventions using certain of the present methods that involve gated datasets.

The terms "comprise" (and any form of comprise, such as "comprises" and "comprising"), "have" (and any form of have, such as "has" and "having"), "contain" (and any form of contain, such as "contains" and "containing"), and "include" (and any form of include, such as "includes" and "including") are open-ended linking verbs. Thus, a method, an apparatus, or a system that "comprises," "has," "contains," or "includes" one or more items possesses at least those one or more items, but is not limited to possessing only those one or more items. For example, a method that comprises receiving a position of an instrument reference marker coupled to an instrument; transforming the position into image space using a position of a non-tissue internal reference marker implanted in a patient; and superimposing a representation of the instrument on an image in which the non-tissue internal reference marker appears possesses at least the receiving, transforming, and superimposing steps, but is not limited to possessing only those steps. Accordingly, the method also covers instances where the transforming includes transforming the position into image space using a transformation that is based, in part, on the position of the non-tissue internal reference marker implanted in the patient, and calculating the transformation using image space coordinates of the internal reference marker in the image. The term "use" should be interpreted the same way. Thus, a calculation that uses certain items uses at least those items, but also covers the use of additional items.

Individuals elements or steps of the present methods, apparatuses, and systems are to be treated in the same manner. Thus, a step that calls for creating a dataset that includes images, one of the images (a) depicting a non-tissue internal reference marker, (b) being linked to non-tissue internal reference marker positional information, and (c) being at least 2-dimensional covers the creation of at least such a dataset, but also covers the creation of a dataset that includes images, where each image (a) depicts the non-tissue internal reference marker, and (b) is linked to non-tissue internal reference marker positional information.

The terms "a" and "an" are defined as one or more than one. The term "another" is defined as at least a second or more. The term "coupled" encompasses both direct and indirect connections, and is not limited to mechanical connections.

Those of skill in the art will appreciate that in the detailed description below, certain well known components and assembly techniques have been omitted so that the present methods, apparatuses, and systems are not obscured in unnecessary detail.

Broadly, embodiments of the present methods, apparatuses, and systems enable the use of dynamic imaging modalities in 2-D and 3-D IGI. Specifically, the various embodiments of the present embodiments of the present methods, apparatuses, and systems are useful for allowing a particular image from a set of images depicting dynamic anatomy to be selected, such that the selected image is the most accurate representation of the instantaneous position and orientation of the live anatomy in the operating theatre. The locations of the present reference markers (in the form of vectors, for example) may be synchronized to each image in the set of images, and the positional information of the markers allows a transformation to be calculated between the real world coordinate space and the image space for the purpose of superimposing the live position of one or more instruments onto the selected image. Dynamic anatomy is anatomy that moves significantly with respect to heart beat and/or respiration, such as the heart, lungs, kidneys, liver, and blood vessels.

More specifically, embodiments of the present methods, apparatuses, and systems are useful for the placing and tracking one or more non-tissue internal reference markers within a gross anatomic region of interest that moves periodically with heart beat and respiration, synchronizing the location or locations of those marker locations with images that best describe the specific anatomy of interest in a particular orientation, selecting the image that best describes the anatomy of interest at any given moment in the operating or procedure room, and superimposing iconic representation of one or more instruments on the most accurate image selected after making the appropriate transformation from the tracking space of the instrument to image space. A "non-tissue internal reference marker" is a reference marker, which is sometimes referred to in the art as a "fiducial," that is positioned inside of a patient (e.g., any living being, human or otherwise) and that is not made from the patient's tissue or other living matter. Embodiments of the present methods, apparatuses, and systems may be used in the delivery of various medical therapies including, but not limited to, pacemaker lead placement, coronary stent placement, cardiac radio frequency ablation, lung biopsy, renal stent placement, transjugular intrahepatic porto-systemic shunting, and percutaneous radio frequency ablation of renal masses.

IGI has not made significant inroads into medical procedures involving dynamic anatomy. IGI is suited to, and has been used primarily in, static anatomy medical procedures due to its usage of static imaging modalities such as single frame fluoroscopy, and single volume MRI and CT. While Rasche (i.e., U.S. Pat. No. 6,473,635) discloses certain IGI with dynamic anatomy, his proposed method depends on the patient's ECG data during the operation. That is, Rasche's method involves collecting ECG data as the operation is taking place and, based on a given phase of that ECG data, displaying an image for viewing by the physician. Such an approach will not work if the patient exhibits an irregular ECG pattern due to the medical therapies that are being applied to him. Examples of induced ECG irregularity would occur during pacemaker and implantable cardioverter defibrillator lead placement and radiofrequency ablation of myocytes to cure tachycardia. The present methods, apparatuses, and systems do not rely on ECG data that is taken as an operation takes place in order to select the appropriate pre-operative image to display for the physician.

Further, Rasche requires the use of an external reference probe in calculating "a simple co-ordinate transformation" between actual spatial and image coordinate systems. An external reference marker will never produce the transformation accuracy of an internal reference marker positioned close to the anatomy of interest—as used by the present methods, apparatuses, and systems—due to a moment arm escalation of error.

1. Use of a Gated Image Dataset

FIG. 1 shows one embodiment of a system (system 100) that includes components that can be used to perform image guided interventions using a gated imaging modality, such as ECG-gated MRI, or ECG-gated CT. The figure depicts a patient 10 positioned on an operating table 12 with a physician 14 performing a medical procedure on him.

Specifically, FIG. 1 depicts physician 14 steering a medical instrument 16 through the patient's internal anatomy in order to deliver therapy. In this particular instance, instrument 16 is depicted as a catheter entering the right atrium by way of the inferior vena cava preceded by a femoral artery access point; however, the present systems are not limited to catheter use indications. The position of virtually any instrument may be tracked as discussed below and a representation of it superimposed on the proper image, consistent with the present methods, apparatuses, and systems. An "instrument" is any device controlled by physician 10 for the purpose of delivering therapy, and includes needles, guidewires, stents, filters, occluders, retrieval devices, and leads. Instrument 16 is fitted with one or more instrument reference markers 18. A tracker 20 (which is sometimes referred to in the art as a "tracking system") is configured to track the type of reference marker or markers coupled to instrument 16. Tracker 20 can be any type of tracking system, including but not limited to an electromagnetic tracking system. An example of a suitable electromagnetic tracking system is the AURORA electromagnetic tracking system, commercially available from Northern Digital Inc. in Waterloo, Ontario Canada. If tracker 20 is an electromagnetic tracking system, element 20 would represent an electromagnetic field generator that emits a series of electromagnetic fields designed to engulf patient 10, and reference marker or markers 18 coupled to medical instrument 16 could be coils that would receive an induced voltage that could be monitored and translated into a coordinate position of the marker(s).

An external reference marker 22 can be placed in a location close to the region of the patient where the procedure is to be performed, yet in a stable location that will not move (or that will move a negligible amount) with the patient's heart beat and respiration. If patient 10 is securely fixed to table 12 for the procedure, external reference marker 22 (which may be described as "static") can be affixed to table 12. If patient 10 is not completely secured to table 12, external reference marker 22 can be placed on region of the back of patient 10 exhibiting the least amount of movement. Tracker 20 can be configured to track external reference marker 22.

One or more non-tissue internal reference markers 24 can be placed in the gross region where the image guided navigation will be carried out. Non-tissue internal reference marker(s) 24 should be placed in an anatomic location that exhibits movement that is correlated with the movement of the anatomy intended for image guided navigation. This location will be internal to the patient, in the gross location of the anatomy of interest.

Medical instrument 16, instrument reference marker(s) 18, external reference marker 22, and non-tissue internal reference marker(s) 24 can be coupled to converter 26 of system 100. Converter 26, one example of which may be referred to in the art as a break-out box, can be configured to convert analog measurements received from the reference markers and tracker 20 into digital data understandable by image guidance computing platform 30, and relay that data to image guidance computing platform 30 to which converter 26 can be coupled. Image guidance computing platform 30 can take the form of a computer, and may include a monitor on which a representation of one or more instruments used during the IGI can be displayed over an image of the anatomy of interest.

System 100 also includes a periodic human characteristic signal monitor, such as ECG monitor 32, which can be configured to receive a periodic human characteristic signal. For example, ECG monitor 32 can be configured to receive an ECG signal in the form of the ECG data transmitted to it by ECG leads 34 coupled to patient 10. The periodic human characteristic signal monitor (e.g., ECG monitor 32) can also be configured to relay a periodic human characteristic signal (e.g., ECG data) to image guidance computing platform 30, to which it can be coupled.

Prior to the start of the image guided intervention, non-tissue internal reference marker(s) 24—but not necessarily static external reference marker 22—should be placed in the gross region of interest for the procedure. After placement of non-tissue internal reference marker(s) 24, patient 10 is to be scanned with an imaging device, such as gated scanner 40, and the resulting gated image dataset transferred to image guidance computing platform 30, to which the imaging device is coupled and which can reside in the operating or procedure theatre. Examples of suitable imaging devices, and more specifically suitable gated scanners, include ECG-gated MRI scanners and ECG-gated CT scanners. A hospital network 50 may be used to couple gated scanner 40 to image guidance computing platform 30.

The imaging device (e.g., gated scanner 40) can be configured to create a gated dataset that includes pre-operative images, one or more of which (up to all) are taken using the imaging device and are linked to a sample of a periodic human characteristic signal (e.g., a sample, or a phase, of an ECG signal). Once patient 10 is scanned using the imaging device and the gated dataset is transferred to and received by image guidance computing platform 30, patient 10 can be secured to operating table 12 and the equipment making up system 100 (e.g., tracker 20, converter 26, image guidance computing platform 30, ECG monitor 32, and gated scanner 40) set up as shown in FIG. 1. Information can then flow among the system 100 components.

Figure 2:
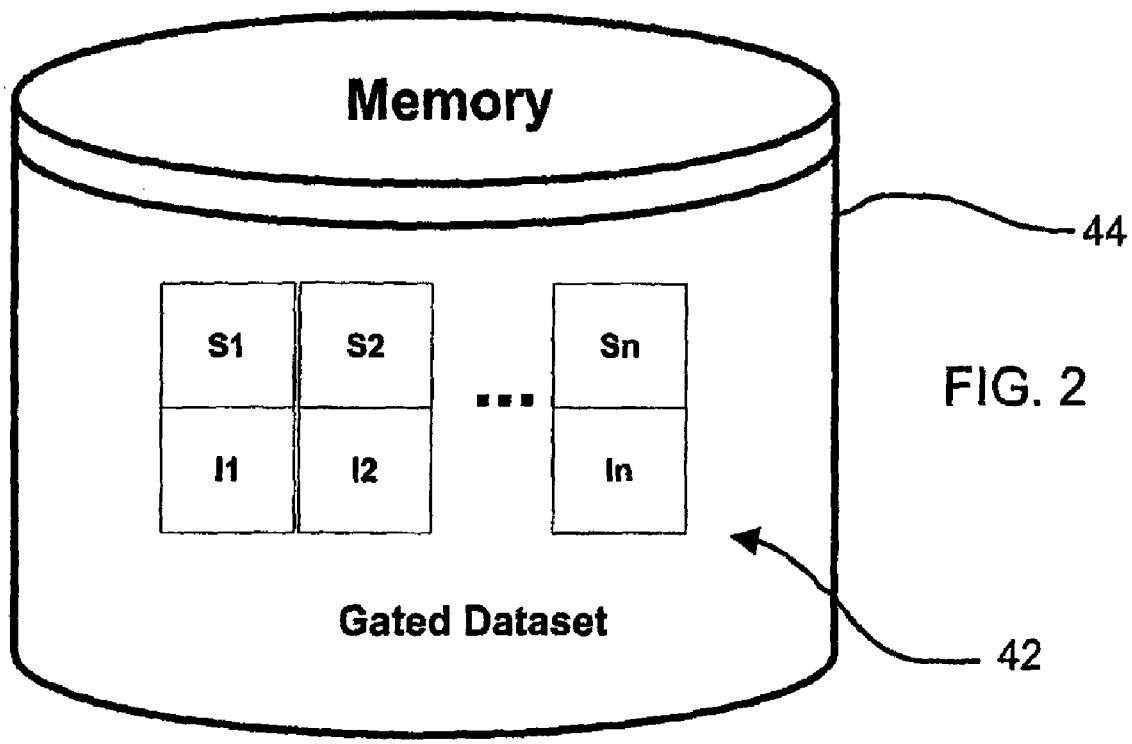
FIG. 2 is a representation of one of the present gated datasets stored in memory.
Figure 3:
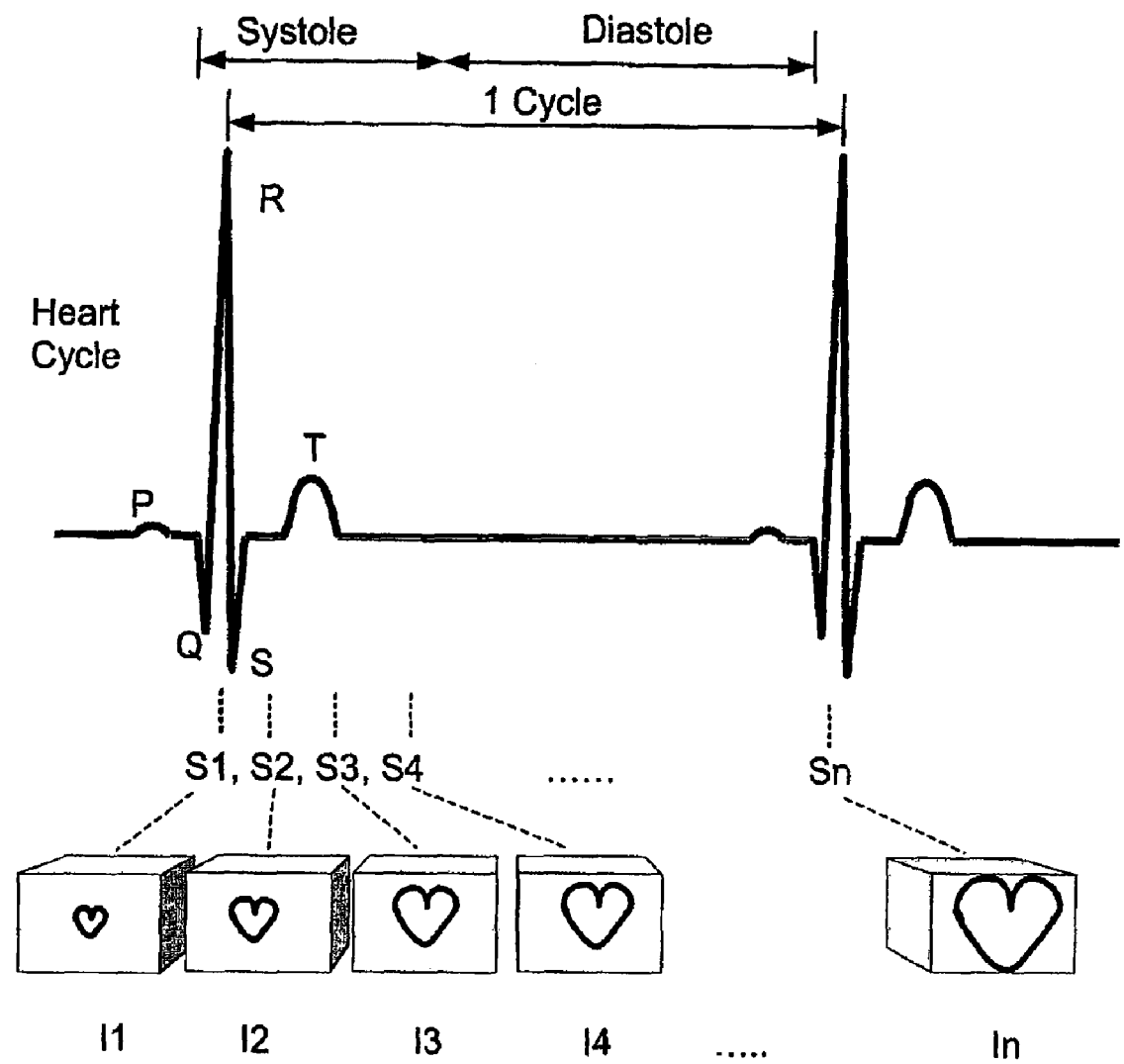
FIG. 3 illustrates one example of samples of a periodic human characteristic signal (specifically, an ECG waveform) associated, or gated, with images of dynamic anatomy.

At this point, a gated dataset created by gated scanner 40 resides on image guidance computing platform 30. FIG. 2 shows gated dataset 42 residing in memory 44, which can reside in image guidance computing platform 30. Gated dataset 42 is organized as a set of images (I1, I2, I3, I4 . . . In) that are correlated with periodic human characteristic signal samples (S1, S2, S3 . . . Sn). In the embodiment shown, the periodic human characteristic signal is taken to be an ECG signal, or waveform. FIG. 3 highlights the relationship between the samples (S1 . . . Sn) and the images (I1 . . . In) that were captured by gated scanner 40. Designations P, Q, R, S, and T are designations well known in the art; they designate depolarizations and re-polarizations of the heart. Gated scanner 40 essentially creates an image of the anatomy of interest at a particular instant in time during the anatomy's periodic movement. Image I1 corresponds to the image that was captured at the S1 moment of patient 10's ECG cycle. Similarly, I2 is correlated with S2, and In with Sn.

Figure 4:
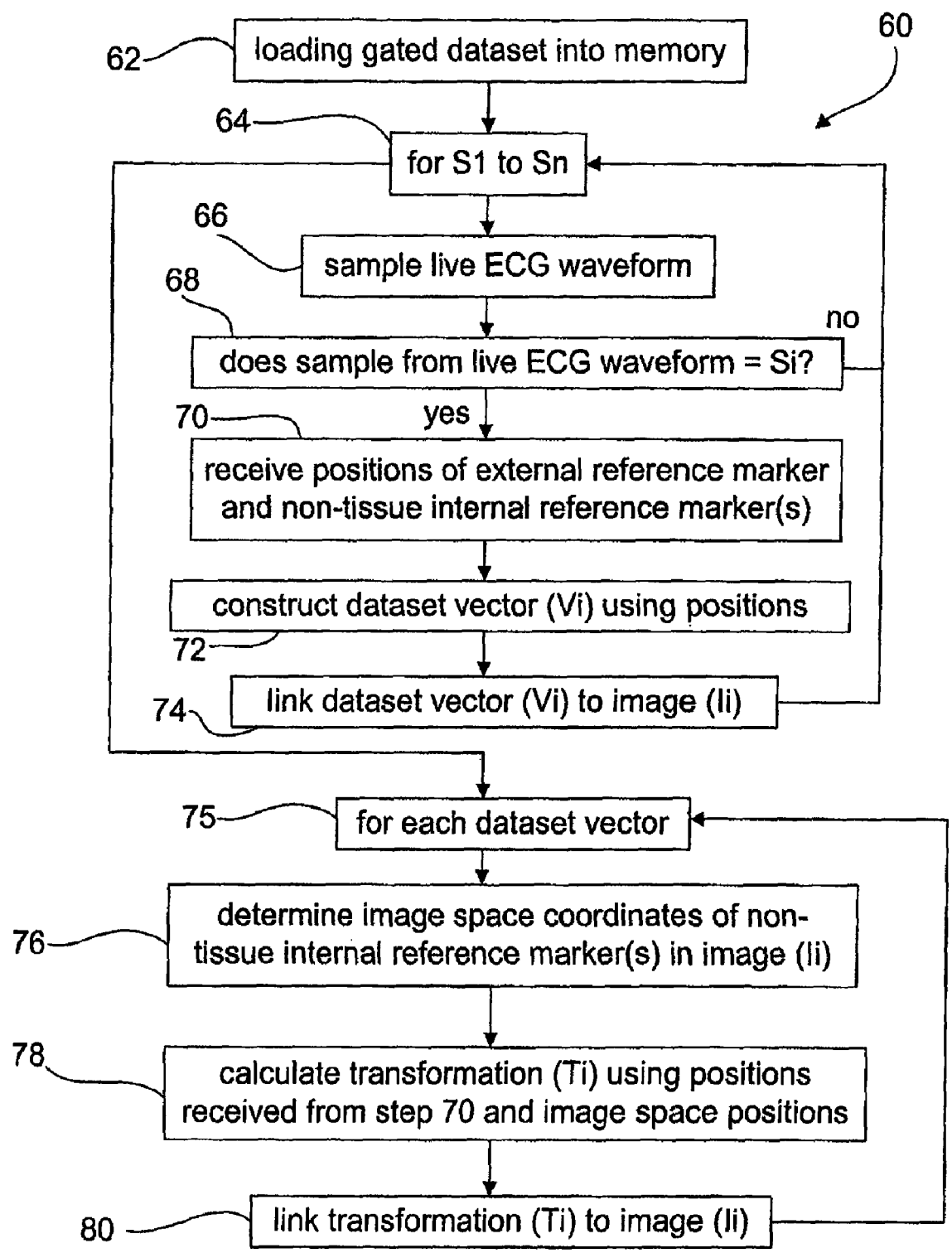
FIG. 4 is a flowchart showing an embodiment of a state through which the present software may run to perform certain embodiments of the present methods.

After the gated scanning has occurred and the system 100 components are coupled to each other as shown in FIG. 1, software running on image guidance computing platform 30 can begin its operation sequence. The software first enters a Calibration State as depicted in FIG. 4. The goal of the software during the Calibration State is to construct a dataset (which, in at least one embodiment, may be described as a look-up table) with dataset vectors linked to the pre-operative images collected by the gating scanner 40. In later states of operation, the look-up table will allow the software to choose the image that best describes the actual instantaneous orientation of the live anatomy. Each dataset vector is a magnitude and direction constructed by examining the location of static external reference marker 22 and non-tissue internal reference marker(s) 24. In this regard, static external reference marker 22 can act as an origin for a dataset vector that begins at origin and ends at the internal reference marker(s) 24 location. (Multiple vectors may be used if there are multiple non-tissue internal reference markers.)

FIG. 4 shows the flow of the Calibration State 60. At step 62, the software can load gated dataset 42 into memory 44 (as depicted in FIG. 4). Next, the software can loop through each gated signal sample (S1, S2 . . . Sn) while sampling the live periodic human characteristic signal coming from patient 10 by way of the periodic human characteristic signal monitor (e.g., ECG monitor 32). In the example shown in the figures, that signal is, like the first periodic human characteristic signal used in constructing the gated dataset, an ECG signal or waveform. Thus, element 64 represents each gated signal sample for which step 66—sampling of the live ECG waveform—occurs. At step 68, the software compares the sample from patient 10's live ECG waveform and compares it to the gated signal sample in question (Si). When the software gets a match (e.g., when the sample from the live ECG waveform matches gated signal sample Si), it can, at step 70, poll tracker 20 to obtain the positions of static external reference marker 22 and non-tissue internal reference marker(s) 24 in order to, at step 72, construct, or calculate, a dataset vector (Vi). A match can be ascertained using signal processing techniques that, in the case of the ECG waveform, examine historical waveform amplitudes. Once the dataset vector is constructed, at step 74, the dataset vector can be stored in the look-up table with a pointer to the image (Ii) that corresponded with the gated signal sample (Si) of gated dataset 42. That is, the dataset vector can be linked to, or associated with, that particular image (Ii). After the software has looped through all the gated signal samples (S1 . . . Sn) of gated dataset 42, constructed a dataset vector (V1 . . . Vn) for each sample, and linked that dataset vector with the appropriate image (I1 . . . In), the software is ready to move on. At this time, the periodic human characteristic signal monitor (e.g., ECG monitor 32) may be turned off or otherwise removed from system 100—it is no longer needed. In at least one embodiment, the dataset vectors described above may comprise nothing more than the tracking space coordinates of the external reference marker 22 and non-tissue internal reference marker(s) 24; as a result, step 72 is not needed, and the linking of the dataset vectors to the various images of gated dataset 42 will comprise linking the tracking space coordinates of the relevant reference markers to those images.

The final step of Calibration State 60 is a transformation calculation step. The software will file through each dataset vector in the look-up table, as noted by element 75, and examine each mapped image. At step 76, the image space coordinates of non-tissue internal reference marker(s) 24 in each image (Ii) will be determined. For example, each image (Ii) can undergo a thresh-holding segmentation that will allow the software to find the image space coordinates of non-tissue internal reference marker(s) 24 in that image. Once the image space coordinates (e.g., voxel, volumetric pixel, coordinates) of non-tissue internal reference marker(s) 24 are known, the positions (e.g., the tracking space positions) of the external reference marker 22 and the non-tissue internal reference marker(s) 24 received at step 70 can be used to calculate a transformation (using a least squares method) between the tracking space and the image space. Step 78 is the calculation of such a transformation (Ti), and step 80 is the linking of the transformation (Ti) to the image (Ii) in question. As a result of that linking, the look-up table will comprise a dataset that includes pre-operative images, at least one the images (and, moreover, each image) depicting non-tissue internal reference marker(s) 24, being linked to a dataset vector and a transformation, and being at least 2-dimensional.

Figure 5:
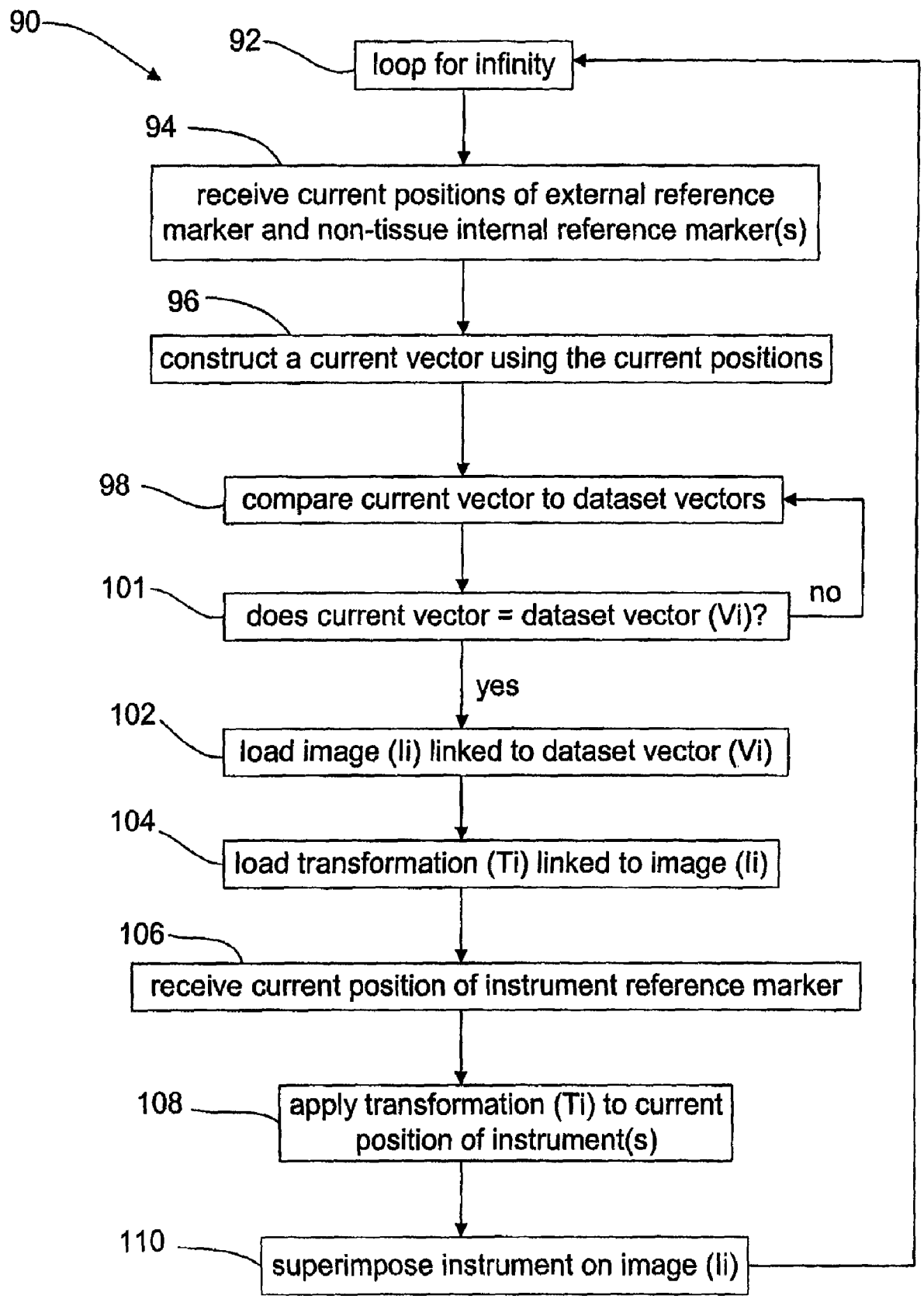
FIG. 5 is a flowchart showing another embodiment of a state through which the present software may run to perform certain embodiments of the present methods.

After completion of Calibration State 60, the software moves the system into Navigate State 90 as depicted in FIG. 5. In this state, the software can enter an infinite loop of events, as designated by element 92. The first step in the loop, step 94, image guidance computing platform 30 can poll the tracker 20 via converter 26 in order to obtain the current position of external reference marker 22 and the current position of non-tissue internal reference marker(s) 24. (It should be understood that "current" in this context is not limiting, and does not mean "instantaneous" or the like; instead, "current" is simply an adjective used to differentiate between the positions received at this step in the present methods from the positions received earlier, for example.) The software can then, at step 96, construct a current vector (here, again, "current" is non-limiting) using the current positions received at step 94. At step 98, the software can compare the current vector to the dataset vectors (V1 . . . Vn) (or will compare just the current positions to the tracking space coordinates) in search of the dataset vector closest to the current vector in question. Upon finding, at step 101, a match dataset vector—defined as the dataset vector (Vi) (or tracking space coordinates) most similar to the current vector (or current positions, or coordinates)—the software can, at step 102, load (e.g., into memory) the image (Ii) from gated dataset 42 pointed to by the matching look-up table dataset vector (Vi). At step 104, the software can also load (e.g., into memory) the transformation (Ti) associated with the dataset vector (Vi) and the correlated image (Ii). At step 106, the system can poll tracker 20 to obtain, via converter 26, the position of instrument reference marker(s) 18. The software can, at step 108, apply the transformation (Ti) to the position of the instrument reference marker(s) 18 to transform that position into image space. At step 110, the software can superimpose (e.g., render, draw, etc.) a representation (e.g., an iconic representation) of instrument 16 (or instruments, as the case may be) on the selected image (Ii) to be displayed on a monitor of image guidance computing platform 30.

The Navigation State 90 steps can be repeated continuously and their performance will provide physician 14 with a live representation of his instruments with respect to the instantaneous position and orientation of the anatomy in question as he image guides those instruments to their correct locations to deliver medical therapy.

A basic embodiment of the present methods that may be achieved using the system 100 software described above is a method that includes creating a dataset that includes images, at least one of the images: depicting a non-tissue internal reference marker, being linked to non-tissue internal reference marker positional information (such as a dataset vector), and being at least 2-D. In another embodiment, and as described above, each image in the dataset depicts a non-tissue internal reference marker (e.g., marker(s) 24), and is linked to non-tissue internal reference marker positional information. The non-tissue internal reference marker positional information may, for example, take the form of positional coordinates or a dataset vector. The images may be 3-D CT images or 3-D MRI images. Other embodiments of the present methods include taking one or more additional steps from among those steps described above. Thus, and by way of example, another embodiment of the present methods includes loading a gated dataset into memory that includes the images, at least one of the images depicting the non-tissue internal reference marker and being linked to a sample of a periodic human characteristic signal. In still another embodiment, each image in the gated dataset depicts the non-tissue internal reference marker and is linked to a sample of the periodic human characteristic signal.

Another basic embodiment of the present methods that may be achieved using the system 100 software described above is a method that includes receiving a position of an instrument reference marker coupled to an instrument (e.g., a medical instrument); transforming the position into image space using a position of a non-tissue internal reference marker implanted in a patient; and superimposing a representation of the instrument on an image in which the non-tissue internal reference marker appears. In another embodiment, the transforming includes transforming the position into image space using a transformation that is based, in part, on the position of the non-tissue internal reference marker implanted in the patient. And in yet another embodiment, the method also includes calculating the transformation using image space coordinates of the internal reference marker in the image. Other embodiments of the present methods include taking one or more additional steps from among those steps described above.

Periodic human characteristic signals other than ECG signals may be used consistently with the steps described above. For example, respiration or hemodynamic characteristics of patient 10 could just as easily be used as periodic human characteristic signals. If such signals are used, appropriate periodic human characteristic signal monitors should be used as well. Furthermore, any imaging modality (not just CT or MRI) that can be gated to a periodic human characteristic signal may be used consistently with the steps described above, including positron emission tomography (PET), ultrasound, and functional MRI (fMRI).

2. Use of CINE Fluoroscopy

Figure 6:
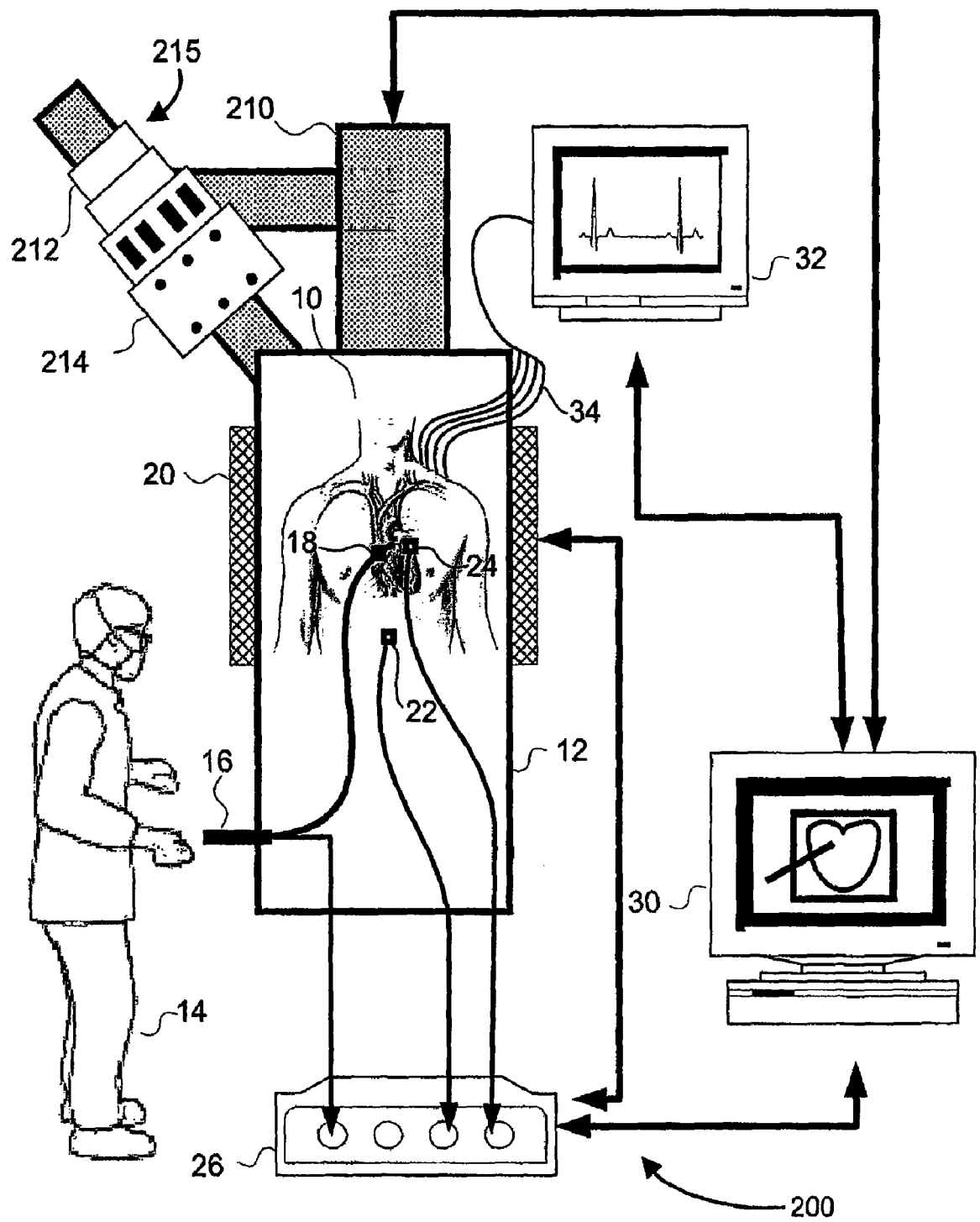
FIG. 6 shows the layout of a system that may be used to carry out image guided interventions using certain of the present methods that do not involve gated datasets.

FIG. 6 depicts one embodiment of a system (system 200) that includes components (many of which are the same, and are coupled in the same fashion, as those in system 100) that can be used to perform image guided interventions using CINE 2-D fluoroscopy as an imaging modality. Gated scanner 40 and hospital network 50 in system 100 are replaced with fluoroscope 215, which, as shown, can include fluoroscope stand 210, fluoroscope receiver unit 212 (e.g., a fluoroscope radiation receiver unit), and fluoroscope calibration jig 214. Fluoroscope 215 is coupled to image guidance computing platform 30.

Figure 7:
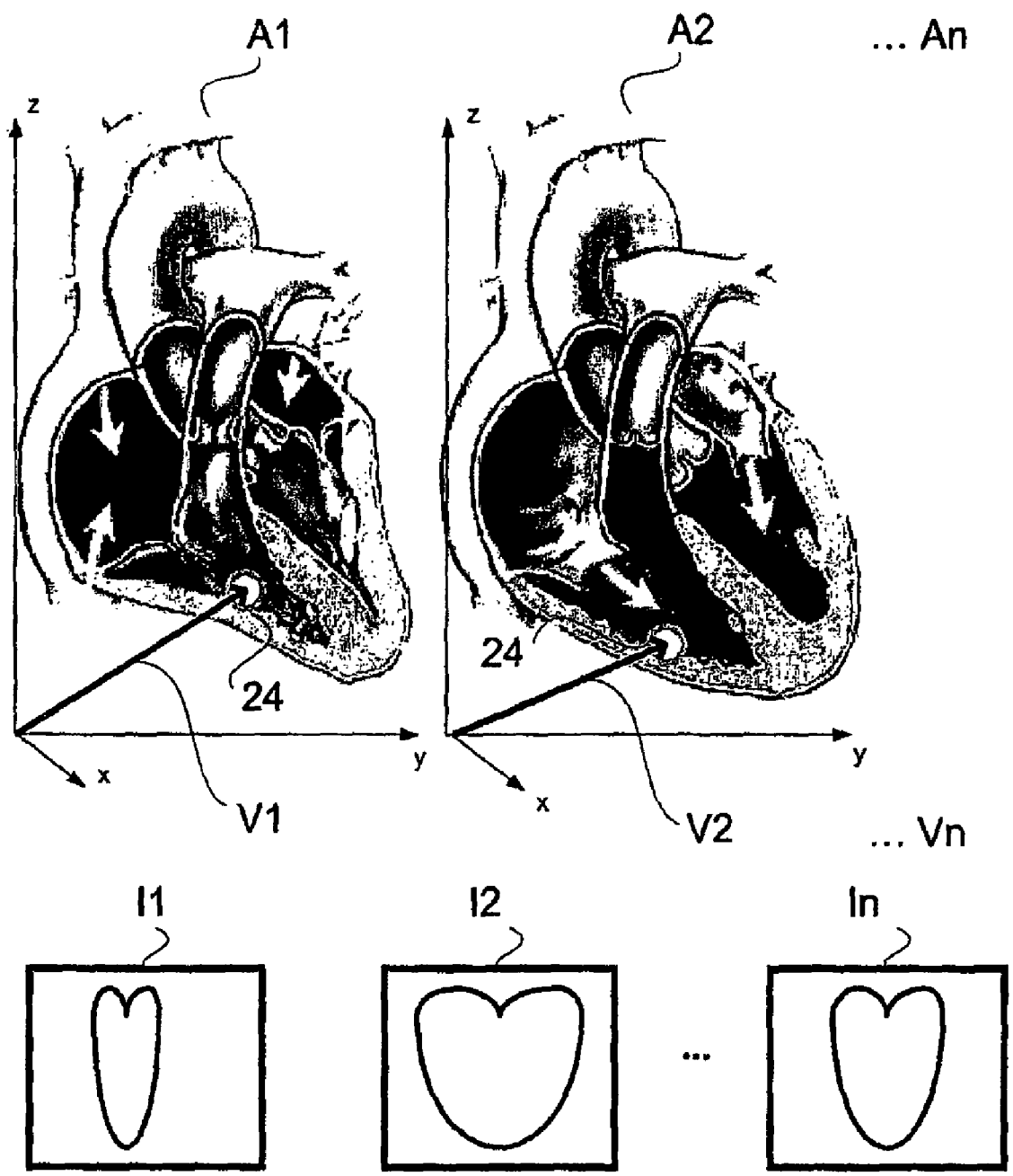
FIG. 7 illustrates one example of the link between reference marker positional information and images of dynamic anatomy.

One advantage of using CINE fluoroscopy as an image guidance modality is that it can be captured during the procedure in the operating or procedure theatre. As a result, the physician may dispense with the gating of a periodic human characteristic signal to pre-operative images. Generally speaking, FIG. 7 captures what will happen using CINE fluoroscopy; a non-tissue internal reference marker(s) 24 will be placed as described above and tracked as each image (I1, I2 . . . In) is captured using fluoroscope 215, and more specifically fluoroscope receiver unit 212. The placement of such internal reference markers is shown in FIG. 7 with respect to the heart, and more specifically, with respect to various stages of the heart's function (A1, A2 . . . An). Vectors (V1, V2 . . . Vn) that are based on the positions of an external reference marker (not shown) and non-tissue internal reference marker 24 (shown) are depicted in FIG. 7 in terms of the X, Y, and Z axis information. Those vectors will be discussed in more detail below. After the image capture process is complete, the particular image most accurately depicting the anatomy at a particular instant can be ascertained by examining the position of the non-tissue internal reference marker(s) and selecting the image that was captured when the marker was last in that particular location and orientation.

To begin the image guided intervention, patient 10 will be placed upon operating table 12 and an ECG monitor 32 will likely be connected to patient 10 for diagnostic purposes unrelated to performing image guidance. Fluoroscope 215 can be positioned to allow images to be captured of patient 10 (likely in an orientation that physician 14 is most comfortable with, such as a Right Anterior Oblique (RAO) view). Physician 14 can place an external reference marker 22 as discussed above (e.g., in the procedural field on a location that does not move with respect to heartbeat and respiration). One or more non-tissue internal reference marker(s) 24 can be placed in the gross region of the anatomy intended for image guidance. Fluoroscope calibration jig 214 can be coupled to fluoroscope receiver unit 212. All connections between fluoroscope 215, reference markers 22 and 24, converter 26, and image guidance computing platform 30 can be fulfilled as depicted in FIG. 6, and information can then flow among the system 200 components.

Figure 8:
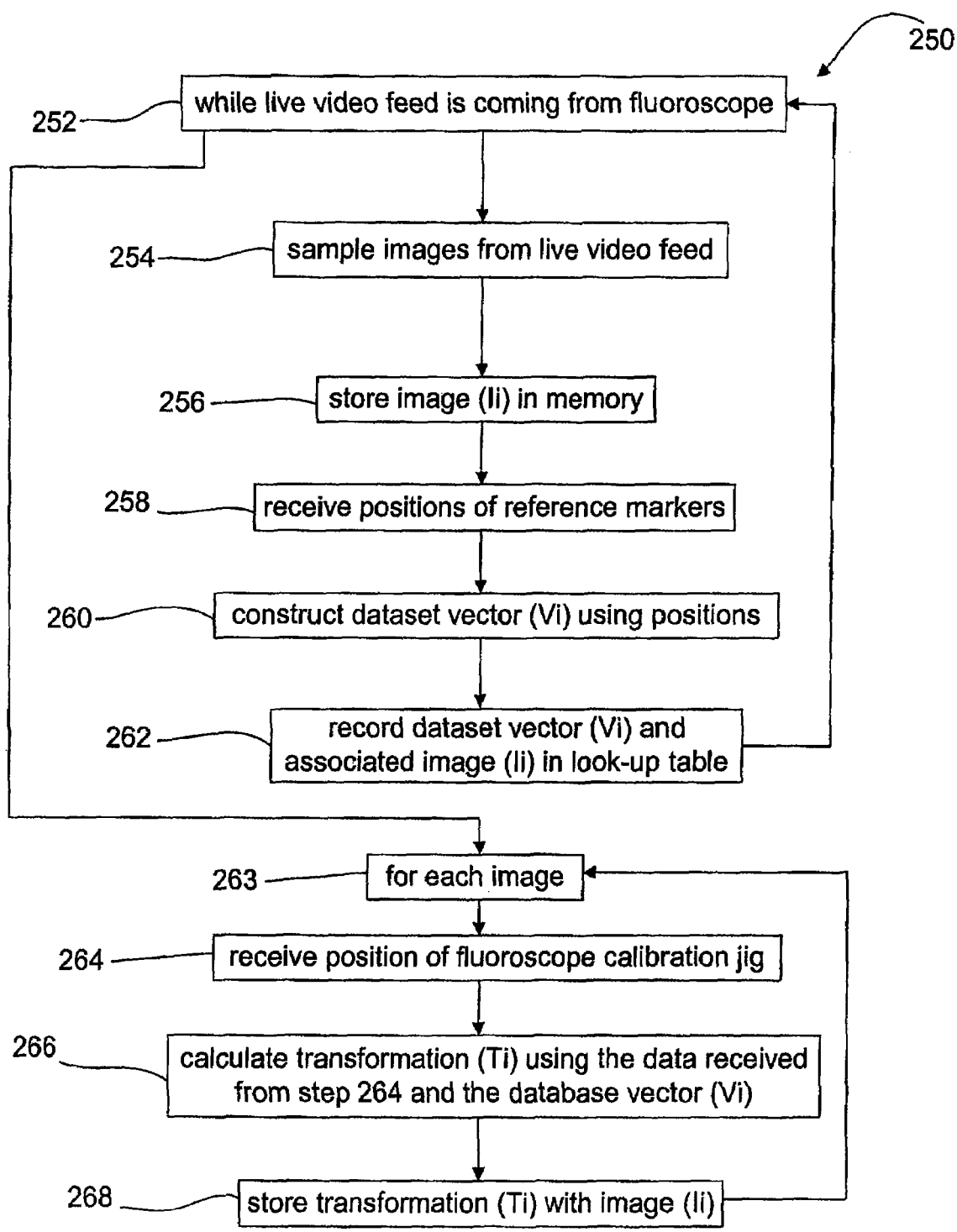
FIG. 8 is a flowchart showing another embodiment of a state through which the present software may run to perform certain embodiments of the present methods.
Figure 10:
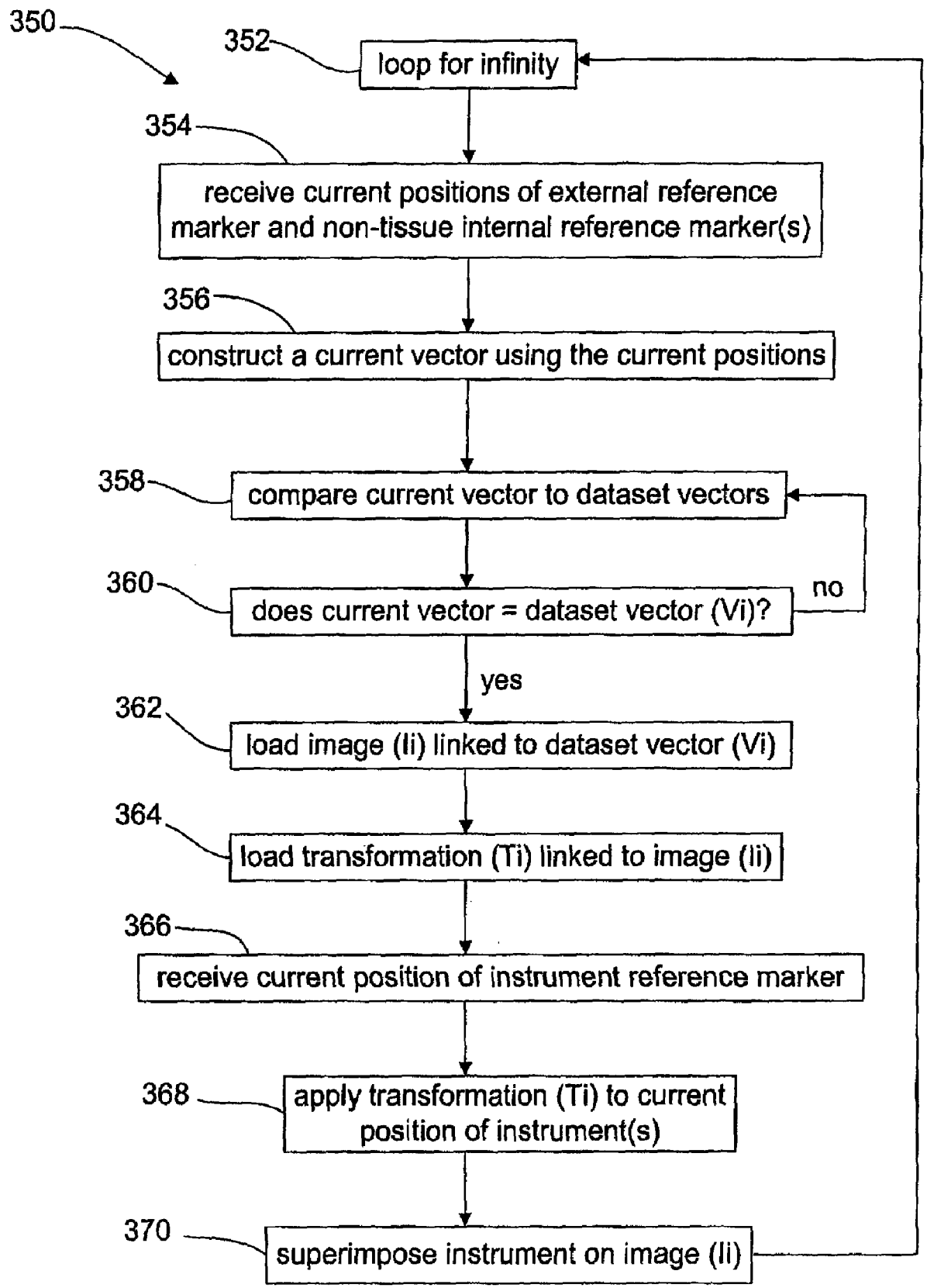
FIG. 10 is a flowchart showing another embodiment of a state through which the present software may run to perform certain embodiments of the present methods.

At this time, system 200 is ready to enter the Calibration State 250 as depicted in FIG. 8. First, physician 14 can trigger fluoroscope 215 to begin acquiring an image signal (e.g., a CINE fluoroscopy loop). As fluoroscope 215 begins to acquire the image signal, the live video feed can be sent to, and received by, image guidance computing platform 30.

While fluoroscope 215 is acquiring the CINE loop, as noted with element 252, the software can, as step 254 notes, sample the live video feed. Sampling consistent with step 254 can occur at a rate greater than 30 Hz so as capture enough images (e.g., image frames) such that they will, when pieced together, appear to be real time to the human eye. As computing power makes faster sampling rates for more feasible, a sampling rate greater than 60 Hz can be implemented in accordance with Nyquist's Law.

Figure 9:
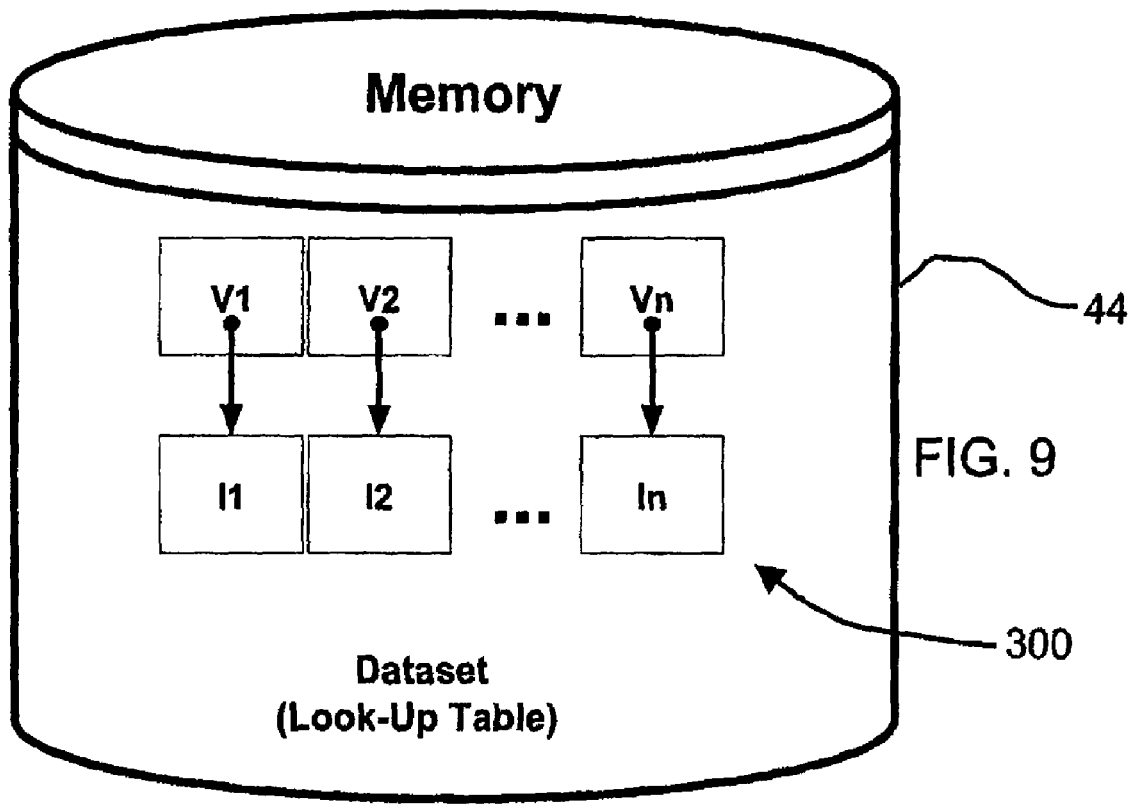
FIG. 9 is a representation of one of the present datasets stored in memory.

The software can create an image (e.g., an image frame) (Ii) as denoted in FIG. 7 and, at step 256, store that image into memory. The software can also poll the tracker 20 and receive, at step 258, positional information for (e.g., the positions of) the reference markers (e.g., static external reference marker 22 and non-tissue internal reference marker(s) 24). The system can then, at step 260, construct, or calculate, a dataset vector (see V1 . . . Vn in FIG. 7) defining the orientation of the reference markers during the instantaneous acquisition of this particular image (Ii). The software can, at step 262, record the dataset vector (Vi) (or at least the positional information) and the associated image (Ii) in a dataset (e.g., dataset 300, which can, in at least one embodiment, take the form of a look-up table) as depicted in FIG. 9. Step 262 may also be described as creating a dataset that includes at least one image that depicts a non-tissue internal reference marker, is linked to positional information about the non-tissue internal reference marker, and is at least 2-D. FIG. 9 shows dataset 300 residing in memory 44, which can reside in image guidance computing platform 30. After a sufficient number of images have been collected and stored, the software begin the transformation calculation process. For example, for each image (Ii), as noted by element 263, the software can, at step 264, poll tracker 20 for, and can receive, the position of the fluoroscope calibration jig 214. With this positional information, the software can, at step 266, calculate a transformation (Ti) from tracking space (e.g., the tracker field coordinate space) to image space (e.g., the fluoroscope image space) using the methods disclosed in U.S. Pat. No. 6,470,207. At step 268, the transformation (Ti) can be stored in association with (e.g., linked to) the image (Ii) in the look-up table associated with, or keyed by, database vector (Vi). This step may also be described as associating the transformation (Ti) with image (Ii). The software can repeat this process until a complete set of images necessary to characterize the anatomy over its entire periodic cycle of movement have been captured and characterized.

After completion of Calibration State 250, the software moves the system into Navigate State 350. In this state, the software can enter an infinite loop of events, as designated by element 352. In the first step in the loop, step 354, image guidance computing platform 30 polls the tracker 20 via converter 26 in order to obtain the current position of external reference marker 22 and the current position of non-tissue internal reference marker(s) 24. (It should be understood that "current" in this context is not limiting, and does not mean "instantaneous" or the like; instead, "current" is simply an adjective used to differentiate between the positions received at this step in the present methods from the positions received earlier, for example.) The software can then, at step 356, construct a current vector (here, again, "current" is non-limiting) using the current positions received at step 354. At step 358, the software can compare the current vector to the dataset vectors (V1 ... Vn) (or will compare just the current positions to the tracking space coordinates) in search of the dataset vector closest to the current vector in question. Upon finding, at step 360, a match dataset vector—defined as the dataset vector (Vi) (or tracking space coordinates) most similar to the current vector (or current positions, or coordinates)—the software can, at step 362, load (e.g., into memory) the image (Ii) from dataset 300 pointed to by the matching look-up table dataset vector (Vi). At step 364, the software can also load (e.g., into memory) the transformation (Ti) associated with the dataset vector (Vi) and the correlated image (Ii). At step 366, the system can poll tracker 20 to obtain, via converter 26, the position of instrument reference marker(s) 18. The software can, at step 368, apply the transformation (Ti) to the position of the instrument reference marker(s) 18 to transform that position into image space. At step 370, the software can superimpose (e.g., render, draw, etc.) a representation (e.g., an iconic representation) of instrument 16 (or instruments, as the case may be) on the selected image (Ii) to be displayed on a monitor of image guidance computing platform 30.

The Navigation State 350 steps can be repeated continuously and their performance will provide physician 14 with a live representation of his instruments with respect to the instantaneous position and orientation of the anatomy in question as he image guides those instruments to their correct locations to deliver medical therapy.

A basic embodiment of the present methods that may be achieved using the system 200 software described above is a method that includes creating a dataset that includes images, at least one of the images: depicting a non-tissue internal reference marker, being linked to non-tissue internal reference marker positional information (such as a vector), and being at least 2-D. In another embodiment, and as described above, each image in the dataset depicts a non-tissue internal reference marker (e.g., marker(s) 24), and is linked to non-tissue internal reference marker positional information. The non-tissue internal reference marker positional information may, for example, take the form of positional coordinates or a dataset vector. The images may be 2-D fluoroscopy images (e.g., CINE fluoroscopy images). Other embodiments of the present methods include taking one or more additional steps from among those steps described above. Thus, and by way of example, another embodiment of the present methods includes calculating a dataset vector using a position of an external reference marker and a position of a non-tissue internal reference marker.

Another basic embodiment of the present methods that may be achieved using the system 200 software described above is a method that includes receiving a position of an instrument reference marker coupled to an instrument (e.g., a medical instrument); transforming the position into image space using a position of a non-tissue internal reference marker implanted in a patient; and superimposing a representation of the instrument on an image in which the non-tissue internal reference marker appears. In another embodiment, the transforming includes transforming the position into image space using a transformation that is based, in part, on the position of the non-tissue internal reference marker implanted in the patient. And in yet another embodiment, the method also includes calculating the transformation using image space coordinates of the internal reference marker in the image. Other embodiments of the present methods include taking one or more additional steps from among those steps described above.

3. Non-Tissue Internal Reference Marker

Figure 11:
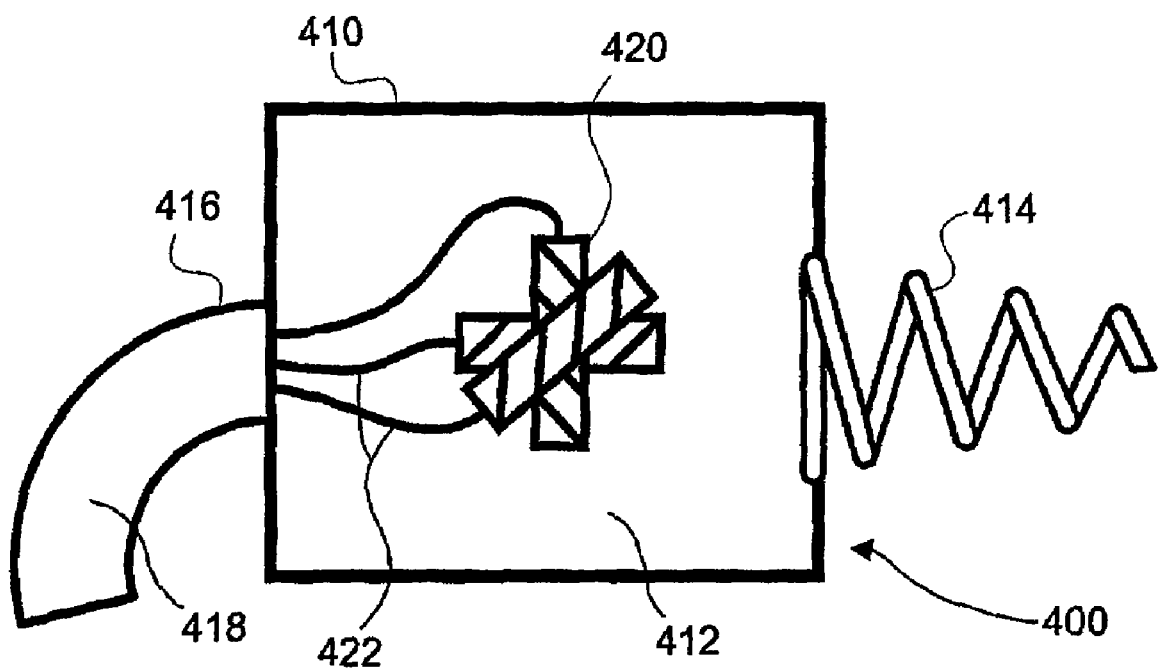
FIG. 11 illustrates an embodiment of one of the present non-tissue internal reference markers.

An example of a non-tissue internal reference marker suitable for use as non-tissue internal reference marker 24 for use with system 100 is shown in FIG. 11. In the case where the imaging modality used for the purposes of image guided intervention is MRI, the non-tissue internal reference marker(s) 24 placed into the patient can be non-ferrous to meet safety requirements of the imaging device (e.g., gated scanner 40). FIG. 11 depicts such an apparatus. Apparatus 400 includes a non-ferrous body (i.e., a body that is not made of any iron) 410 that defines a chamber 412. Body 410 can be made of a material that makes it opaque to the imaging modality such that it shows up as a blank (white) spot on the image. Such materials include platinum and titanium. A non-ferrous tissue fixation member 414 is coupled (e.g., through attachment) to body 410 at an end of body 410 to allow apparatus 400 to be implanted in the gross region of interest for a procedure. Member 414, as shown, can have a pig-tail shape. As a result, member 414 can be unscrewed to release the apparatus after completion of the procedure. Such pig-tail designs are common among temporary pacing leads in the field of cardiac electrophysiology. The embodiment of apparatus 400 shown in FIG. 11 also includes a segment 416 (such as a sheath, or a portion of a sheath) coupled to body 410. Segment 416 includes a passageway 418 that is in communication with chamber 412. The segment can be plastic. Any portion of segment 418 that extends outside of a patient is not considered to be a part of any of the present non-tissue internal reference markers.

When apparatus 400—as a non-tissue internal reference marker—is implanted prior to imaging, chamber 412 can remain empty. The patient into which the apparatus is implanted can be scanned with apparatus 400 implanted and segment 418 in place, which can extend outside of the patient (e.g., outside of the patient's skin). Upon successful completion of the scan, one or more ferrous tracking sensors 420 that are configured for placement in chamber 412 and their ferrous connecting leads 422 (e.g., wires) can be introduced into chamber 412 via segment 416 and locked into place. This apparatus, therefore, alleviates the need for the tracking sensors to be non-ferrous.

As will be understood by those having skill in the art and the benefit of this disclosure, the steps disclosed above, and the techniques for carrying them out, may be implemented in any number of various media or devices. While described above in terms of software, it should be understood that the referenced software may take the form of machine (e.g., computer) readable instructions on computer readable media. The computer-readable, or machine-readable media, may take many forms, including any data storage device that can store data that can afterwards be read by a computer or a computer system, including a disk, such as a floppy disk, a zip disk, or the like; a server; read-only memory; random access memory; CD-ROMs; a memory card; magnetic tape; optical data storage devices, SMARTMEDIA® cards; flash memory; compact flash memory; and the like. The computer readable medium can also be distributed over network-coupled computer systems so that the computer readable instructions are stored and executed in a distributed fashion. For example, the computer readable medium may take the form of a carrier wave such as, for example, signals on a wire (e.g., signals downloaded from the Internet) or those that are transmitted electromagnetically or through infra red means. Furthermore, when the machine readable instructions in question have been loaded onto a given machine, that machine can be described as configured to take whatever actions are defined by the instructions.

In another embodiment, any of the present methods may be embodied in an integrated circuit, such as application specific integrated circuit (ASIC), or in a field programmable gate array (FPGA). In another embodiment, any of the present methods may be embodied by a combination of hardware and software; for instance, certain instructions may be executed by a chip running appropriate firmware. In another embodiment, any of the present methods may be embodied by a kit, such as a software developer's kit. Such a kit may include not only software, but also any corresponding hardware to execute the software. For instance, a kit may include a computer board along with drivers and software to be run by that board. Those having skill in the art will recognize that the present methods may be implemented by other means known in the art to achieve an identical or similar result. All such means are considered to be within the scope of the present methods and systems that include devices configured to carry out the present methods.

The claims are not to be interpreted as including means-plus- or step-plus-function limitations, unless such a limitation is explicitly recited in a given claim using the phrase(s) "means for" or "step for," respectively.

I claim:

1. A non-transitory processor-readable medium storing code representing instructions to cause a processor to perform a process, the code comprising code to:
   create a dataset that includes a plurality of images associated with a body part, at least one image from the plurality of images depicting a non-tissue internal reference marker, the at least one image from the plurality of images being associated with a non-tissue internal reference marker position information, the at least one image from the plurality of images being at least 2-dimensional;
   calculate for each image in the dataset a dataset vector based on a position of the non-tissue internal reference marker and the position of an external reference marker;
   receive data associated with a current position of the external reference marker and a current position of the non-tissue internal reference marker;
   calculate a current vector using the data associated with the current position of the external reference marker and the data associated with a current position of the non-tissue internal reference marker;
   identify a match dataset vector (MDV), the MDV being the dataset vector most similar to the current vector, the MDV being associated with an image from the dataset;
   receive data associated with a current position of an instrument reference marker coupled to an instrument;
   apply a transformation associated with the image associated with the MDV to the current position of the instrument reference marker, thus transforming the current position of the instrument reference marker into image space; and
   superimpose a representation of the instrument on the image associated with the MDV.

2. The non-transitory processor-readable medium of claim 1, wherein the code to create the dataset includes code to create a dataset that includes at least one image taken via at least one of fluoroscopy, CINE fluoroscopy, computed tomography (CT), magnetic resonance imaging (MRI), ultrasound, positron emission tomography (PET), or functional magnetic resonance imaging (fMRI).

3. The processor-readable medium of claim 1, wherein the code to create the dataset includes code to create a dataset that includes at least one 3-dimensional image.

4. The processor-readable medium of claim 1, wherein code to create the dataset includes code to create a dataset that includes a plurality of images including gated information.

5. The processor-readable medium of claim 1, further comprising code to:
   cause threshold segmentation of each image of the plurality of images, the threshold segmentation allowing the code to create the dataset.

6. The processor-readable medium of claim 1, further comprising code to:
   receive a periodic human characteristic signal.

7. The processor-readable medium of claim 6, wherein the code to receive the periodic human characteristic signal includes code to receive a human characteristic signal calculated using the position of the non-tissue internal reference marker.

8. The processor-readable medium of claim 1, wherein the code to create the dataset includes code to create a dataset that includes at least one image from the plurality of images depicting a non-tissue internal reference marker placed on the body part.

9. The processor-readable medium of claim 1, wherein the code to create a dataset includes code to create a dataset that includes at least one image from the plurality of images depicting a non-tissue internal reference marker placed on the body part, the body part exhibiting movement correlated with at least one of heartbeat or respiration.

10. The processor-readable medium of claim 1, wherein the code to create a dataset includes code to create a dataset that includes at least one image from the plurality of images depicting a non-tissue internal reference marker placed on the body part, the body part exhibiting cyclical movement.

11. A method, comprising:
   creating a dataset that includes a plurality of images associated with a body part, at least one image from the plurality of images depicting a non-tissue internal reference marker, the at least one image from the plurality of images being associated with non-tissue internal reference marker positional information, the at least one image from the plurality of images being at least 2-dimensional;
   calculating for each image in the dataset a dataset vector based on a position of the non-tissue internal reference marker and the position of an external reference marker;

receiving data associated with a current position of the external reference marker and a current position of the non-tissue internal reference marker;

calculating a current vector using the data associated with the current position of the external reference marker and the data associated with a current position of the non-tissue internal reference marker;

identifying a match dataset vector (MDV), the MDV being the dataset vector most similar to the current vector, the MDV being associated with an image from the dataset;

receiving data associated with a current position of an instrument reference marker coupled to an instrument;

applying a transformation associated with the image associated with the MDV to the current position of the instrument reference marker, thus transforming the current position of the instrument reference marker into image space; and superimposing a representation of the instrument on the image associated with the MDV.

12. The method of claim 11, wherein the creating the dataset that includes a plurality of images associated with a body part includes creating a dataset that includes at least one image taken via at least one of fluoroscopy, CINE fluoroscopy, computed tomography (CT), magnetic resonance imaging (MRI), ultrasound, positron emission tomography (PET), or functional magnetic resonance imaging (fMRI).

13. The method of claim 11, wherein the creating the dataset includes creating a dataset that includes at least one 3-dimensional image.

14. The method of claim 11, wherein creating the dataset includes creating a dataset that includes a plurality of images including gated information.

15. The method of claim 11, further comprising:
causing threshold segmentation of each image of the plurality of images, the threshold segmentation allowing the code to create the dataset.

16. The method of claim 11, further comprising:
receiving a periodic human characteristic signal.

17. The method of claim 16, wherein the receiving the periodic human characteristic signal includes receiving a human characteristic signal calculated using the position of the non-tissue internal reference marker.

18. The method of claim 11, wherein the creating the dataset includes creating a dataset that includes at least one image from the plurality of images depicting a non-tissue internal reference marker placed on the body part.

19. The method of claim 11, wherein the creating the dataset includes creating a dataset that includes at least one image from the plurality of images depicting a non-tissue internal reference marker placed on the body part, the body part exhibiting movement correlated with at least one of heartbeat or respiration.

20. The method of claim 11, wherein the creating a dataset includes creating a dataset that includes at least one image from the plurality of images depicting a non-tissue internal reference marker placed on the body part, the body part exhibiting cyclical movement.

* * * * *